United States Patent [19]

Habermeier et al.

[11] 4,202,987
[45] May 13, 1980

[54] BIS-ANTHRANILATES

[75] Inventors: Jürgen Habermeier, Pfeffingen; Roland Moser, Basel; Wolfgang Seiz, Pfeffingen, all of Switzerland

[73] Assignee: Ciba-Geigy Corporation, Ardsley, N.Y.

[21] Appl. No.: 966,424

[22] Filed: Dec. 4, 1978

[30] Foreign Application Priority Data

Dec. 9, 1977 [CH] Switzerland ............... 15121/77

[51] Int. Cl.$^2$ ............... C07C 101/54; C08G 59/54
[52] U.S. Cl. ............... 560/49; 528/68; 528/84; 528/123; 528/365; 525/453
[58] Field of Search ............... 560/49

[56] References Cited

U.S. PATENT DOCUMENTS

| | | | |
|---|---|---|---|
| 2,620,352 | 12/1952 | Beatty | 560/49 |
| 3,817,940 | 6/1974 | Blahak et al. | 560/50 |
| 3,929,863 | 12/1975 | Blahak et al. | 560/50 |
| 3,975,428 | 8/1976 | Blahak et al. | 560/49 |
| 4,007,239 | 2/1977 | Blahak et al. | 560/50 |
| 4,069,309 | 1/1978 | Ciaudelli et al. | 560/49 |

FOREIGN PATENT DOCUMENTS

| | | | |
|---|---|---|---|
| 847680 | 2/1977 | Belgium . | |
| 847681 | 2/1977 | Belgium . | |
| 1073464 | 6/1967 | United Kingdom | 560/49 |

OTHER PUBLICATIONS

Sherwin-Williams Technical Bulletin, 152, p. 4.
Elastomerics, Mar. 1977, pp. 37–42.

*Primary Examiner*—Joseph E. Evans
*Assistant Examiner*—G. T. Breitenstein
*Attorney, Agent, or Firm*—Joseph F. DiPrima

[57] ABSTRACT

Novel bis-anthranilates are obtained by reacting 1 mol of a N,N'-bis-(hydroxyalkyl)-urea with 2 mols of isatoic anhydride. The novel bis-anthranilates are valuable chain extenders for polyurethanes and valuable crosslinking agents for polyurea and epoxide resins.

4 Claims, No Drawings

BIS-ANTHRANILATES

The present invention relates to novel bis-anthranilates of bis-(hydroxyalkyl)-ureas, processes for their preparation and their use as chain extenders and crosslinking agents in the preparation of polyurethanes and polyurea resins or as curing agents for epoxide resins.

4,4'-Methylene-bis-(o-chloroaniline) (MOCA) has for a long time been one of the best chain extenders and crosslinking agents introduced in polyurethane and polyurea technology since MOCA, especially in the preparation of polyurethane elastomers or flexible foams, has favourable processing properties in respect to reactivity and, moreover, imparts outstanding mechanical properties to the crosslinked polymers. However, as is known, there is a suspicion that MOCA may be carcinogenic (cf. "Elastomerics", March 1977, page 37) and there has been no lack of attempts to replace MOCA by crosslinking agents which are equivalent in respect of the most favourable processing characteristics and end characteristics of the polymers.

In Technical Bulletin 152 of the "Sherwin-Williams Company" (USA), bis-anthranilates of linear aliphatic diols are mentioned. In "Elastomerics", March 1977, page 37 et seq., 4,4'-methylene-bis-anthranilates are proposed as a replacement for MOCA. Furthermore, in the two Belgian Patent Specifications 847,680 and 847,681 bis-anthranilates of diols containing a N,N-heterocyclic radical, for example 1,3-di-(2'-hydroxyethyl)-benzimidazolone and 1,3-di-(2'-hydroxyethyl)-5,5-dimethylhydantoin, are disclosed as chain extenders for polyurethanes.

It has now been found that when bis-anthranilates of N,N'-bis-(hydroxyalkyl)-ureas are used as chain extenders and crosslinking agents in urethane and urea formulations, elastomers with better mechanical strength are obtained.

The present invention thus relates to novel bis-anthranilates of the formula I

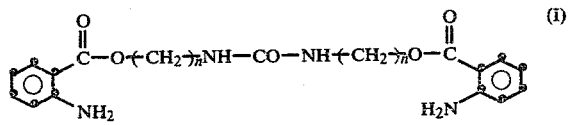

in which each n is the number 2, 3 or 4.

In the formula I, each n is preferably 2 or 3, especially 2.

The compounds of the formula I can be prepared by reacting 1 mol of a bis-(hydroxyalkyl)-urea of the formula II

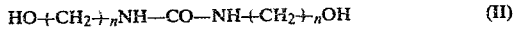

in which the two n's are as defined in formula I, with 1.8 to 2.5 mols of isatoic anhydride, preferably in the presence of a basic catalyst, to give compounds of the formula I.

The starting materials used in this process are preferably compounds of the formula II in which n is 2 or 3; in particular N,N'-di-(2-hydroxyethyl)-urea is employed.

In a preferred embodiment, the starting compounds are used in stoichiometric amounts, i.e. 1 mol of the bis-(hydroxyalkyl)-urea of the formula II is reacted with 2 mols of isatoic anhydride.

The compounds of the formula II are known and can be obtained by the process described in Example 1 of U.S. Pat. No. 2,379,261, by reacting urea with the corresponding alkanolamines with the elimination of ammonia. Bis-(hydroxyethyl)-urea can also be prepared from ethanolamine and COS in good yield according to German Auslegeschrift No. 1,468,398.

The compounds of the formula I are preferably prepared in the presence of an organic solvent or solvent mixture. Suitable solvents are, in particular, the aprotic solvents, such as dioxan, chloroform, toluene, dimethylformamide and dimethylacetamide.

When preparing the compounds of the formula I, the reaction temperature can be from 30° to 160° C. Preferably, the reaction is carried out in the temperature range of 50° to 130° C.

Preferably, the conversion reaction is catalysed by bases, and alcoholates, including those of the starting diols, alkali metal hydroxides or alkaline earth metal hydroxides, tertiary amines and ammonium bases or other substances having a basic action can be used. Frequently, basic impurities in the starting materials also suffice. Catalysts can be used in amounts of 0.01 to 10 mol %, based on the amount of isatoic anhydride employed.

Another process for the preparation of the compounds of the formula I comprises esterifying 1 mol of a bis-(hydroxyakyl)-urea of the formula II with 2 mols of o-nitrobenzoic acid and then reducing the nitro groups in a known manner to the amino groups.

The compounds of the formula I can also be prepared by a trans-esterification process, by trans-esterifying the bis-(hydroxyalkyl)-ureas of the formula II with anthranilates, preferably alkyl anthranilates having 1 to 4 C atoms in the alkyl group, the alcohol formed being distilled off.

The compounds, according to the invention, of the formula I are in the main colourless crystalline substances which are readily soluble in many organic solvents, such as dioxan, toluene, benzene, dichlorobenzene and dimethylformamide. Furthermore, the novel compounds also have good solubility in higher molecular weight diols, diol-ether compounds and short-chain polyesters containing hydroxyl groups.

As mentioned initially, the compounds according to the invention are a valuable replacement for 4,4'-methylene-bis-(o-chloroaniline). They can therefore be used in an analogous manner. In particular, the compounds according to the invention are suitable as chain extenders in polyurethanes and as crosslinking agents for the preparation of polyurea resins. In addition, they can be used as curing agents for epoxide resins.

EXAMPLE 1

Bis-anthranilate of N,N'-di-(2-hydroxyethyl)-urea 1 liter of toluene and 250 ml of dimethylformamide are initially introduced into a laboratory reactor which can be heated and is fitted with a stirrer, a thermometer, a reflux condenser and a device for adding pulverulent material. 103.7 g (0.7 mol) of N,N'-di-(2-hydroxyethyl)-urea and 0.59 g of sodium hydroxide powder are introduced, with stirring. The mixture is warmed to 80° C. and the 2-phase reaction mixture is stirred intensively. 239.8 g (1.47 mols) of isatoic anhydride are then added in 6 portions in the course of 6 hours and a vigorous evolution of $CO_2$ starts immediately. A further 0.59 g of sodium hydroxide powder are added after 3 hours and again after 6 hours. After the final addition of isatoic anhydride, the reaction mixture is stirred for a further 3 hours at 80°–90° C. and is then cooled to room temperature and residues of unconverted isatoic anhydride are filtered off. The pale yellow, clear solution is concentrated to dryness and the residue is dried to constant weight under 0.3 mm Hg at 110° C. 272 g of the crude product are obtained in the form of a reddish highly viscous melt. For purification, the crude product is recrystallized from 400 ml of 94% ethanol. This yields 165 g (61% of theory) of colourless crystals which melt between 134° and 147° C. For further purification, the product can be recrystallized from acetone, whereupon the product of analytical purity with a melting point of 148°–150° C. forms.

Elementary Analysis gives for $C_{19}H_{22}N_4O_5$: Found: C 59.05%; H 5.76%; N 14.63%. Calculated: C 59.10%; H 5.70%; N 14.50%.

The IR and H-NMR spectra are in accord with the following structure:

EXAMPLE 3

Bis-anthranilate of 1,3-di-(4′-hydroxy-n-butyl)-urea 6.13 g (0.03 mol) of 1,3-di-(4′-hydroxy-n-butyl)–urea (melting point=125°–127° C.) are initially introduced into 25 ml of toluene and 10 ml of dimethylformamide, at room temperature, analogously to Example 1. 0.06 g of sodium hydroxide powder is added, with stirring, and the mixture is warmed to 80° C. 10.28 g of isatoic anhydride are added in 4 portions in the course of 6 hours. The clear brown solution is then heated at 100° C. for a further 1½ hours.

Working up is carried out analogously to Example 1. 13 g of a liquid, viscous crude product are obtained and this is purified by dissolving in 30 ml of methylene chloride and precipitating from 250 ml of petroleum ether. This yields 11.5 g (86.5% of theory) of the desired product, the 60 Mc H-NMR spectrum of which is in accord with the following structure:

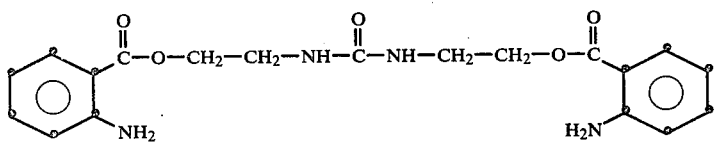

EXAMPLE 2

Bis-anthranilate of 1,3-di-(3′-hydroxy-n-propyl)-urea 2 liters of toleune and 1 liter of dimethylformamide are initially introduced into an apparatus according to Example 1. 441 g (2.5 mols) of 1,3-di-(3′-hydroxy-n-propyl)-urea with a melting point of 94°–96° C. are added, with stirring, and the mixture is warmed to 80° C. 3.2 g (3 mol %) of sodium hydroxide powder are added to the slightly yellowish solution and 856.5 g of isatoic anhydride are then added in 5 portions in the course of 4 hours. The reaction is discerned by the vigorous evolution of $CO_2$. The reaction mixture is then allowed to react for a further 2 hours at 100° C., cooled to room temperature and filtered to remove a small amount of undissolved material and the filtrate is concentrated to dryness at 100° C. The residue is then dried for 3 hours at 120° C., to constant weight. 1,037 g of a crude product which crystallises slowly are obtained.

The crude product can, if necessary, be recrystallised from a mixture of 1.5 liters of acetone and 350 ml of methanol.

This yields 760.3 g (73.5% of theory) of the pure product with a melting point of 125.5°–126.5° C. Analysis by thin layer chromatography shows that the product is pure.

Elementary analysis gives, for $C_{21}H_{26}N_4O_5$: Found: 60.82% C; 6.31% H; 13.52% N. Calculated: 60.86% C; 6.32% H; 13.52% N.

The 60 Mc H-NMR spectrum is also in accord with the structure given below.

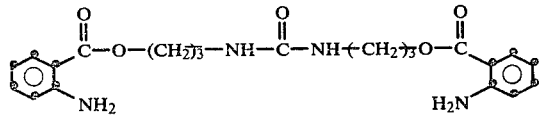

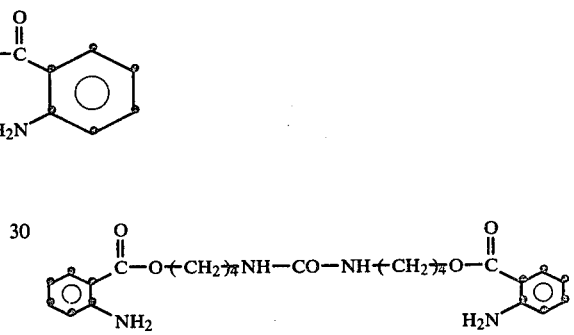

APPLICATION EXAMPLES

Example A

A prepolymer is prepared from 50 g of a low-molecular weight polyester of adipic acid and ethylene glycol, which has hydroxyl end groups and a OH number of 55 (available commercially under the name "Desmophen 2000") and which has previously been freed from traces of water by heating (for 3 hours at 130° C.) in vacuo (0.5 mm Hg), and 25.0 g of 4,4′-diisocyanato-diphenylmethane (available commercially under the name "Desmodur 44 V"), by stirring for 30 minutes at 110° C.

A mixed melt of 30 g of "Desmophen 2000" and 9.3 g of the bis-anthranilate prepared according to Example 1 (dissolved at 130° C. to give a clear solution and then cooled to about 100° C.) is stirred into this prepolymer, which is still at about 100° C.

This casting resin mixture is poured into aluminium moulds with a wall thickness of 4 mm and is cured completely at 140° C. in the course of 5 hours.

Elastomeric mouldings are thus obtained which have a brown coloration originating from "Desmodur 44 V" and have excellent strength.

EXAMPLE B

A prepolymer is prepared in a manner similar to that described in Example A from 70 g of the polyester used in Example A and 34 g of toluylene diisocyanate (available commercially under the name "Desmodur T 100").

This prepolymer is mixed at 100° C. with a homogeneous solution of 30 g of the polyester ("Desmophen 2000") and 9.3 g of the bis-anthranilate prepared according to Example 1.

After curing according to Example A, elastomeric moulded materials are obtained which are colourless to pale yellow and transparent.

Examples C and D

A liquid isocyanate prepolymer which has been pre-pared from toluylene diisocyanate and polytetramethylene glycol and has an isocyanate content of 1.5 equivalents/kg and a viscosity of about 10,000 mPa.s/25° C. (available commercially under the name "Adipren L-167") was mixed with various diamines as crosslinking agents.

The constituents of these mixtures were in each case mixed in the ratios and under the processing conditions indicated in Table 1. The mixtures obtained after intimate mixing were freed in vacuo from the air stirred in and then poured into aluminium moulds, pretreated with mould-release agents, to produce sheets with dimensions of 135×135×4 mm and 135×135×1 mm and crosslinked under the conditions indicated in Table 1.

Test pieces which correspond to Standard DIN 53,455, No. 4 were stamped out from the 4 mm thick sheets using a punch and the tests to determine the tensile strength and elongation at break were carried out on these. The remainder of the 4 mm sheet was used for determining the Shore A hardness (DIN 53,505) and the impact resilience according to DIN 53,455. Shaped pieces for determining the tear propagation resistance according to DIN 53,363 were cut out from the 1 mm thick sheet.

In order to determine the reactivity, gel times were determined on thermostat-controlled hot plates which were set at 100° and 120° C.

The values measured are listed in Table 1.

Table 1

| Example | C | D | Comparison 1 | Comparison 2 |
|---|---|---|---|---|
| Processing conditions, reactivity and end characteristics of the casting resin mixtures | | | | |
| Crosslinking agent (diamine) | bis-anthranilate according to Example 1 | bis-anthranilate according to Example 2 | neopentylglycol dianthranilate* | MOCA |
| Parts of crosslinking agent per 100 parts of prepolymer | 26 | 31 | 25.1 | 16 |
| Gel time at 120° C. (minutes) | 25 | 30 | 33 | 4 |
| 100° C. | 40 | 48 | 1642 | 7 |
| Processing conditions (temperature °C.) Prepolymer | 100 | 70 | 80 | 80 |
| Crosslinking agent | 140 | 120 | 80 | 120 |
| Crosslinking conditions (hours/°C.) | 6/120 | 6/100 | 6/120 | 6/120 |
| Appearance of the elastomer | pale yellow, transparent | pale brown, slightly opaque | brown, transparent | yellow, opaque |
| Shore A hardness (units) | 84 | 83 | 61 | 92 |
| Impact resilience (%) | 21 | 20 | 8 | 26 |
| Tear propagation resistance (N/mm$^2$) | 97 | — | 27 | 100 |
| Tensile strength (N/mm$^2$) | 52 | 49 | 17.8 | 42 |
| Elongation at break (%) | 417 | 480 | 640 | 333 |

*According to German Offenlegungsschrift 2,040,644

EXAMPLE E

An isocyanate prepolymer of low viscosity, which was prepared from toluylene diisocyanate and polypropylene glycol and has a viscosity of 2,000 mPa.s/25° C. and an isocyanate content of 2.7 equivalents/kg, was mixed with the bis-anthranilate according to Example 1 and with MOCA.

The constitutents of these mixtures were in each case mixed under the conditions and in the mixing ratios indicated in Table 2. The preparation and testing of the test pieces were carried out in a manner analogous to that described under Example C. The values measured are listed in Table 2.

Table 2

| Example | E | Comparison 3 |
|---|---|---|
| Processing conditions and end characteristics of the casting resin mixtures | | |
| Crosslinking agent (diamine) | bis-anthranilate according to Example 1 | MOCA |
| Parts of crosslinking agent per 100 parts of prepolymer | 41.2 | 32 |
| Processing conditions (temperature °C.) Prepolymer | 70 | 70 |
| Crosslinking agent | 150 | 120 |
| Crosslinking conditions (hours/°C.) | 6/120 | 6/120 |
| Appearance of the elastomer | pale yellow | yellow |
| Shore A hardness (units) | 98 | 100 |
| Impact resilience (%) | 34 | 23 |
| Tensile strength (N/cm$^2$) | 33 | 20 |
| Elongation at break (%) | 273 | 105 |

EXAMPLES F and G

A liquid, unmodified epoxide resin based on bisphenol A with an epoxide content of 5.4 equivalents/kg and a viscosity of about 10,000 mPa.s/25° C. was mixed in equivalent ratios with the bis-anthranilates prepared in Examples 1 and 2 and the mixtures were melted together and cured under the conditions indicated in Table 3.

4 g amounts of the mixtures thus obtained were poured into small aluminium dishes about 5 cm in diameter. The glass transition temperature of the moulded material obtained after curing was then determined using a Thermoanalyzer (Type TA 2000 from Mettler, Greifensee, Switzerland).

In order to test the adhesive characteristics, the mixtures according to the invention were applied, whilst still in the uncrosslinked state, to the ends of aluminum (Anticorodal B) test strips which had dimensions of 170×25×1.5 mm and had previously been roughened by grinding and degreased by washing with solvent (acetone). In each case two of these test strips were so adjusted with the aid of a gauge that the ends coated with resin/curing agent mixture overlapped by 12 mm. After fixing with a clamp, the adhesive bond was cured and after cooling the clamp was removed and the tensile shear strength was then tested in a tensile test according to DIN 53,183.

A further portion of resin/curing agent mixture was applied to a glass plate and cured in an oven in accordance with the data in Table 3. The chemical resistance of the film thus obtained was determined, the procedure being as follows:

The appearance of the film is described briefly (visual). One drop of each of the particular chemicals is then left on the film for 1 hour. After this period of action, the chemicals are wiped off and the surface of the film graded visually, grade 1 being given for no visible attack, grade 2 for slight attack and grade 3 for severe attack on the surface of the film and grade 4 being given for complete destruction of the film.

Table 3

| Processing conditions and end characteristics of the casting resin mixtures | | |
|---|---|---|
| Example | F | G |
| Curing agent (diamine) | bis-anthranilate according to Example 1 | bis-anthranilate according to Example 2 |
| Parts of curing agent per 100 parts of epoxide resin | 52.1 | 55.9 |
| Processing conditions | melted together at 140° C. | melted together at 100° C. |
| Curing conditions (hours/°C.) | 8/140 | 8/140 |
| Appearance of the moulded material | yellow, transparent | pale brown, transparent |
| Glass transition temperature (°C.) | 100 | 95 |
| Tensile shear strength (N/mm$^2$) | 16.7 | 19.7 |
| Appearance of the film | pale yellow with high gloss | yellow with high gloss |
| Chemical stability towards: | | |
| 5N H$_2$SO$_4$ | 1 | 1 |
| 5N NaOH | 1 | 1 |
| H$_2$O | 1 | 1 |
| Acetone | 2 | 2 |
| Cl-benzene | 1 | 1 |

What is claimed is:

1. A bis-anthranilate of the formula

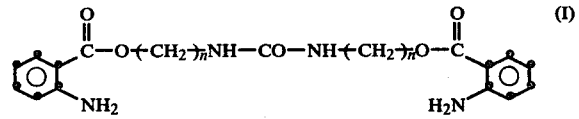

in which each n is the number 2, 3 or 4.

2. A diester according to claim 1, in which each n in the formula I is 2.

3. A diester according to claim 1, in which each n in the formula I is 3.

4. A diester according to claim 1, in which each n in the formula I is 4.

* * * * *